(12) United States Patent
Hurwitz et al.

(10) Patent No.: US 7,874,957 B2
(45) Date of Patent: Jan. 25, 2011

(54) APPARATUS FOR MEASURING EXERCISE PERFORMANCE

(75) Inventors: Elisa Hurwitz, Great Falls, VA (US); Keith W. Brendley, McLean, VA (US)

(73) Assignee: Artis, LLC, Herndon, VA (US)

( * ) Notice: Subject to any disclaimer, the term of this patent is extended or adjusted under 35 U.S.C. 154(b) by 0 days.

(21) Appl. No.: 11/774,305

(22) Filed: Jul. 6, 2007

(65) Prior Publication Data

US 2008/0015089 A1 Jan. 17, 2008

Related U.S. Application Data

(60) Provisional application No. 60/806,631, filed on Jul. 6, 2006.

(51) Int. Cl.
*A63B 71/00* (2006.01)
(52) U.S. Cl. ............................ 482/8; 482/57; 482/63
(58) Field of Classification Search .............. 482/1–9, 482/57, 65, 900–902, 63, 64; 434/247
See application file for complete search history.

(56) References Cited

U.S. PATENT DOCUMENTS

| | | | | |
|---|---|---|---|---|
| 3,848,467 A | * | 11/1974 | Flavell | 482/4 |
| 4,298,893 A | * | 11/1981 | Holmes | 348/730 |
| 4,358,105 A | * | 11/1982 | Sweeney, Jr. | 482/5 |
| 4,378,111 A | * | 3/1983 | Tsuchida et al. | 482/8 |
| 4,408,613 A | * | 10/1983 | Relyea | 600/483 |
| 4,419,890 A | * | 12/1983 | Kotamaki | 73/379.07 |
| 4,436,097 A | * | 3/1984 | Cunningham | 600/520 |
| 4,654,010 A | * | 3/1987 | Havriluk | 434/254 |
| 4,709,917 A | * | 12/1987 | Yang | 482/63 |
| 5,027,303 A | * | 6/1991 | Witte | 702/44 |
| 5,165,278 A | * | 11/1992 | Huszczuk et al. | 73/379.06 |
| 5,213,555 A | * | 5/1993 | Hood et al. | 482/57 |
| 5,246,411 A | * | 9/1993 | Rackman et al. | 482/57 |
| 5,267,925 A | * | 12/1993 | Boyd | 482/64 |
| 5,513,316 A | * | 4/1996 | Rodrigues et al. | 714/38 |
| 5,516,334 A | * | 5/1996 | Easton | 482/8 |
| 5,643,146 A | * | 7/1997 | Stark et al. | 482/63 |
| 5,813,864 A | * | 9/1998 | Ikuta | 434/253 |
| 5,919,115 A | * | 7/1999 | Horowitz et al. | 482/6 |
| 5,947,869 A | * | 9/1999 | Shea | 482/8 |
| 6,059,692 A | * | 5/2000 | Hickman | 482/8 |
| 6,152,856 A | * | 11/2000 | Studor et al. | 482/8 |

(Continued)

OTHER PUBLICATIONS

Expresso S2 bike: http://www.expresso.com/ copyright 2007-1008).

(Continued)

*Primary Examiner*—Loan Thanh
*Assistant Examiner*—Daniel F Roland
(74) *Attorney, Agent, or Firm*—Nixon & Vanderhye PC

(57) ABSTRACT

An integrated sensor apparatus capable of detecting exercise equipment parameters such as power output and cadence is designed so as to be easily retrofittable to existing equipment. To the extent that a particular sensor uses friction measurement, it can supplant an existing friction causing device on the equipment. Additionally, the sensor can communicate, wirelessly if desired, with a processing device. The processing device is capable of receiving and processing a plurality of sensor signals. The processing device can then output processed signals to a display, so that a plurality of people joining in a group exercise or competition can easily track their relative performance in real-time.

15 Claims, 14 Drawing Sheets

U.S. PATENT DOCUMENTS

| | | | |
|---|---|---|---|
| 6,171,218 B1* | 1/2001 | Shea | 482/57 |
| 6,244,988 B1* | 6/2001 | Delman | 482/8 |
| 6,464,618 B1* | 10/2002 | Shea | 482/8 |
| 6,638,198 B1* | 10/2003 | Shea | 482/8 |
| 6,659,916 B1* | 12/2003 | Shea | 482/57 |
| 6,749,537 B1* | 6/2004 | Hickman | 482/8 |
| 6,786,848 B2* | 9/2004 | Yamashita et al. | 482/8 |
| 6,808,472 B1* | 10/2004 | Hickman | 482/8 |
| 6,921,351 B1* | 7/2005 | Hickman et al. | 482/8 |
| 7,044,891 B1* | 5/2006 | Rivera | 482/8 |
| 7,094,184 B1* | 8/2006 | Chen et al. | 482/93 |
| 7,224,326 B2* | 5/2007 | Sefton | 345/8 |
| 2002/0198080 A1* | 12/2002 | Reck | 482/8 |
| 2003/0134714 A1* | 7/2003 | Oishi et al. | 482/6 |
| 2005/0054492 A1* | 3/2005 | Neff | 482/57 |
| 2005/0209049 A1* | 9/2005 | Shields | 482/8 |
| 2005/0233861 A1* | 10/2005 | Hickman et al. | 482/8 |
| 2006/0003872 A1* | 1/2006 | Chiles et al. | 482/57 |
| 2006/0040793 A1* | 2/2006 | Martens | 482/8 |
| 2006/0094569 A1* | 5/2006 | Day | 482/57 |
| 2006/0189439 A1* | 8/2006 | Baudhuin | 482/8 |
| 2006/0234840 A1* | 10/2006 | Watson et al. | 482/61 |
| 2006/0270527 A1* | 11/2006 | Hanaya et al. | 482/57 |
| 2006/0292534 A1* | 12/2006 | Tomes | 434/247 |
| 2007/0042867 A1* | 2/2007 | Lin | 482/8 |
| 2007/0093360 A1* | 4/2007 | Neff et al. | 482/8 |
| 2007/0117680 A1* | 5/2007 | Neff et al. | 482/8 |
| 2007/0197345 A1* | 8/2007 | Wallace et al. | 482/8 |
| 2008/0096725 A1* | 4/2008 | Keiser | 482/8 |
| 2008/0146416 A1* | 6/2008 | Mueller et al. | 482/8 |

OTHER PUBLICATIONS

Vcycling, "Virtual Reality Indoor Cycling," http://www.vcycling.com/pages/home.asp (2006).

Computrainer,RacerMate, http://www.racermateinc.com/computrainer.asp?gclid=CM_GgazK55MCFR8cagoddRJgWw (2006).

Saris/CycleOps, http://www.saris.com/t-ClubIC.aspx?skinid=4 (Saris/CycleOps) (2006).

* cited by examiner

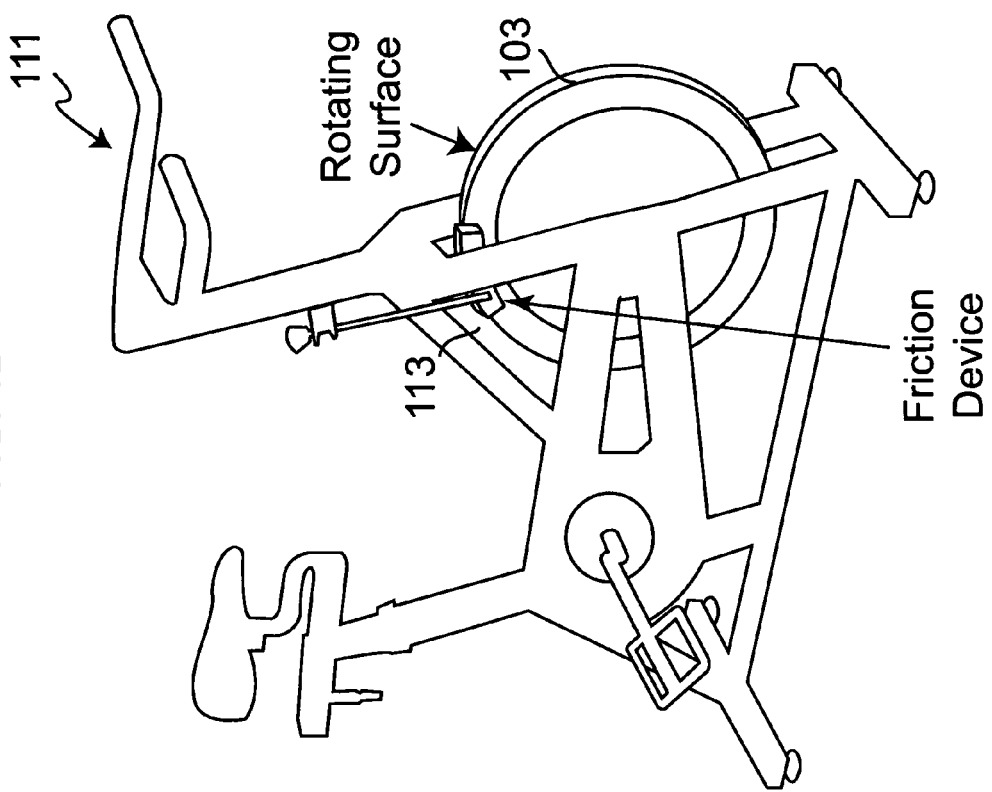
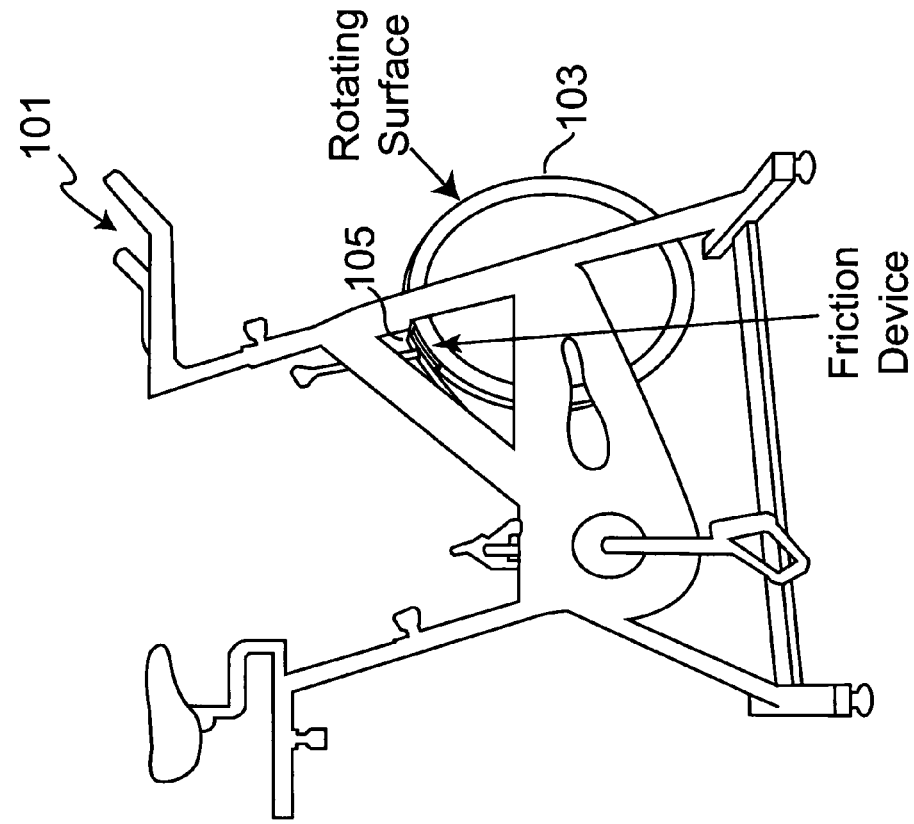

FIG. 4 Exemplary illustrative non-limiting integrated sensor device.

FIG. 5 Example of an integrated sensor device mounted on an exemplary exercise bicycle.

FIG. 6 Generic exemplary illustrative non-limiting integrated force sensor and brake design.

FIG. 7 Optical cadence sensor: With every rotation of the wheel, the light from the emitter will reflect off of the retro-reflector on the wheel back into the detector. The change in signal of the detector can be monitored and converted into a frequency.

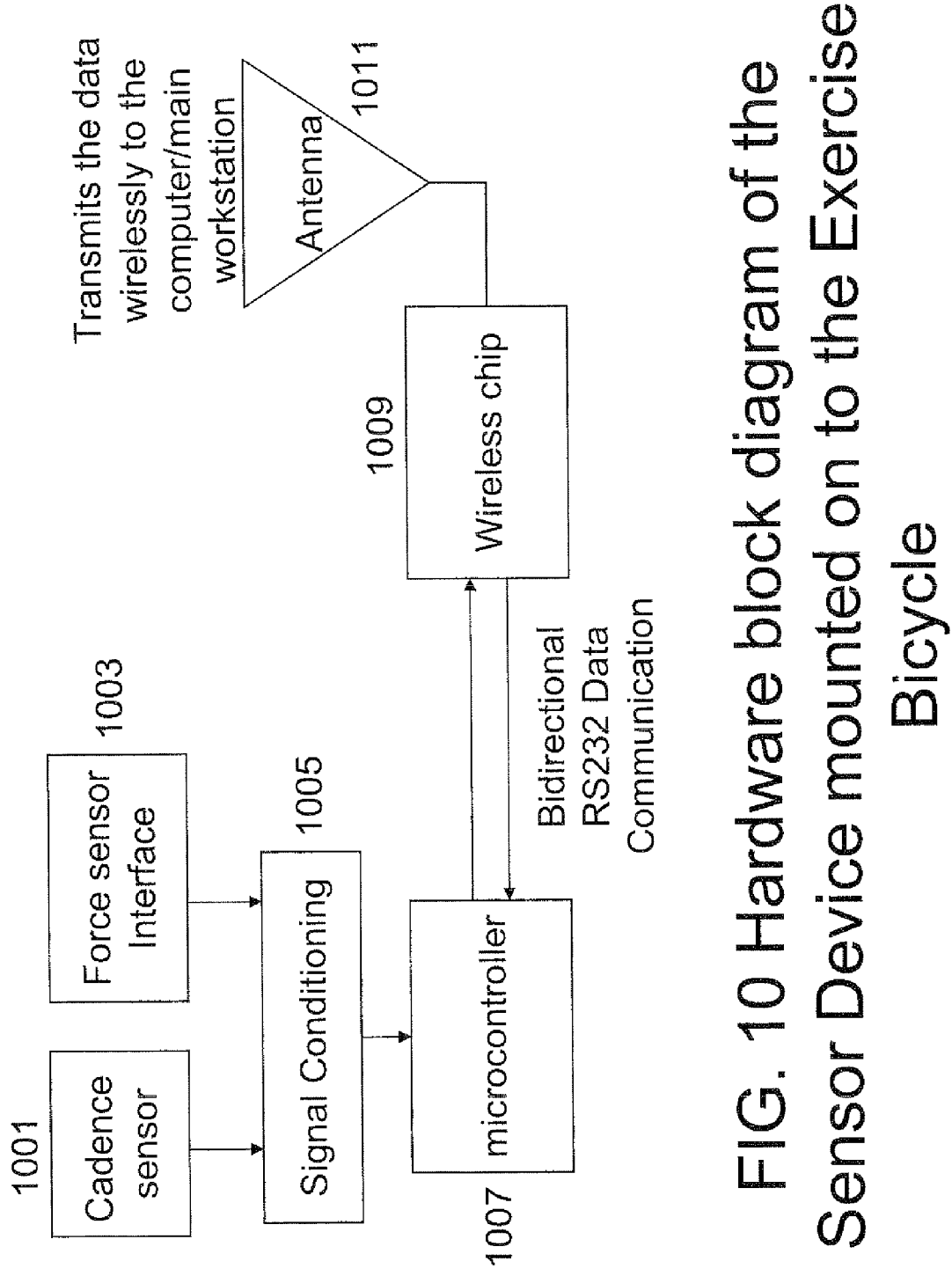
FIG. 10 Hardware block diagram of the Sensor Device mounted on to the Exercise Bicycle

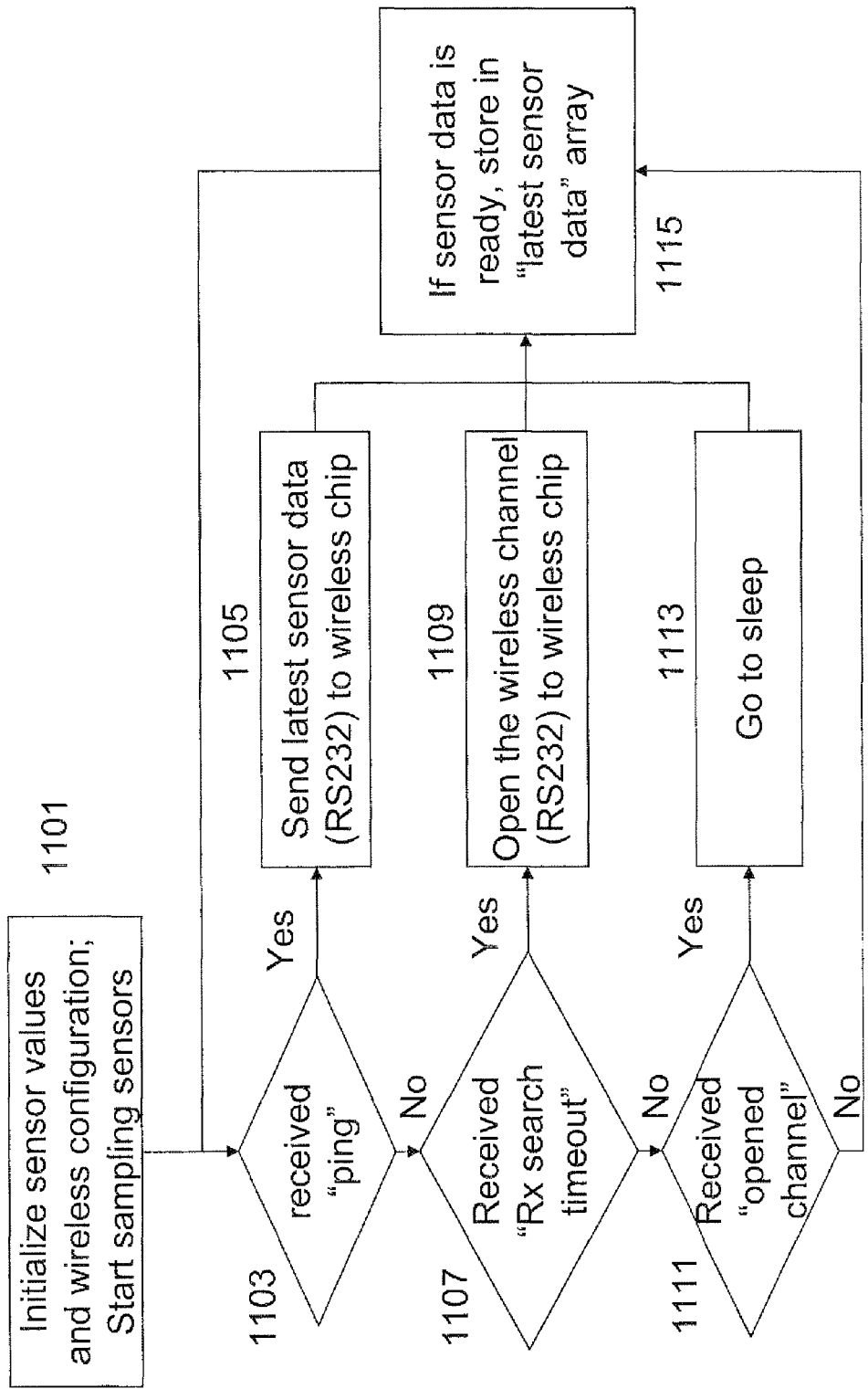
FIG. 11 Embedded Software Flowchart

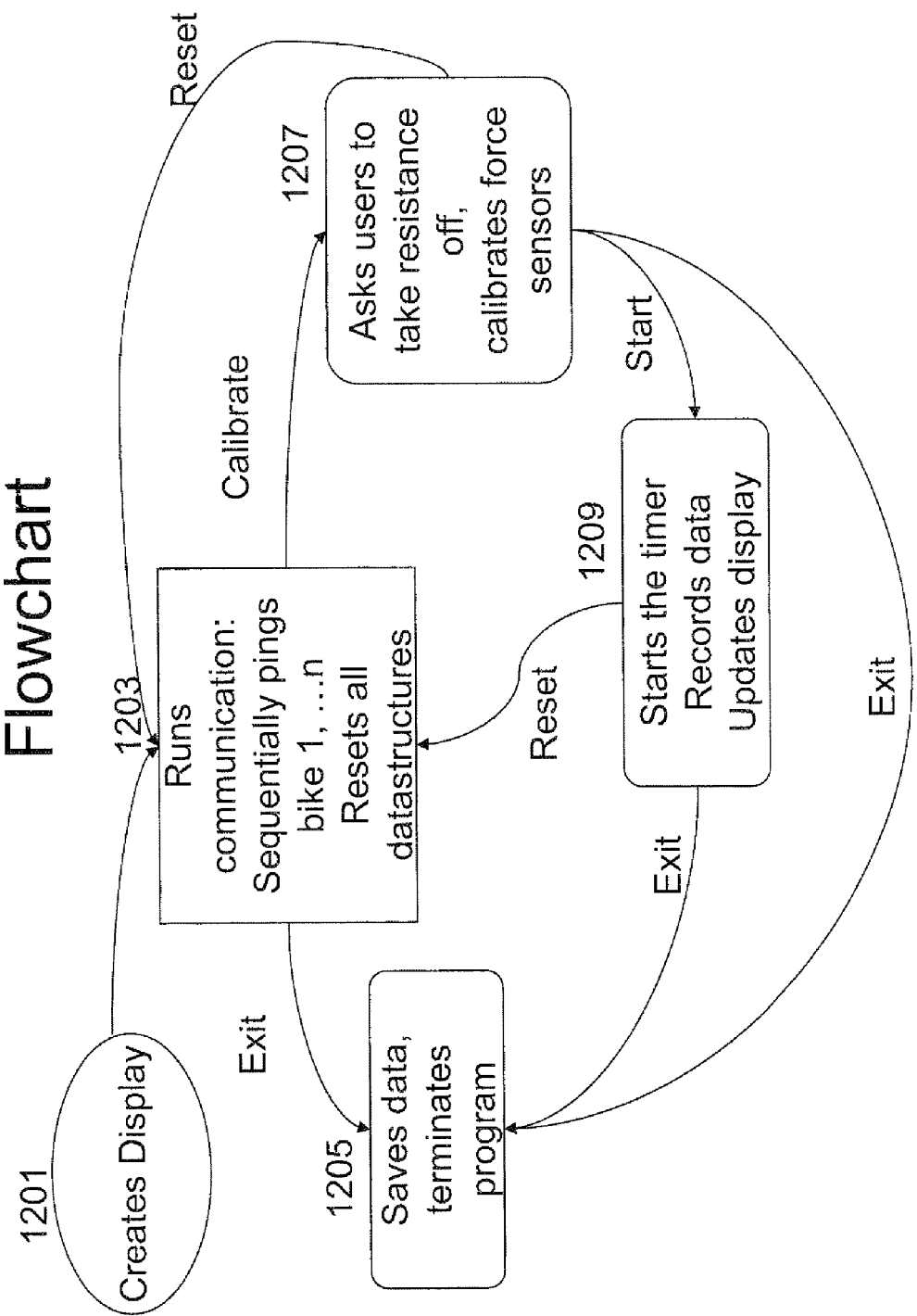
FIG. 12 Main Workstations Software Flowchart

FIG. 13  Star Topology Network
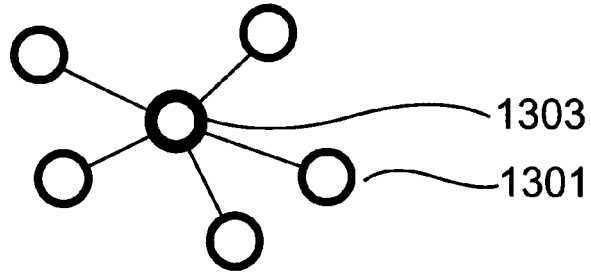
O Reduced Function Device
  (Sensor, Controller, Actuator, etc.)
● PAN Coordinator
FIG. 14  Mesh Network
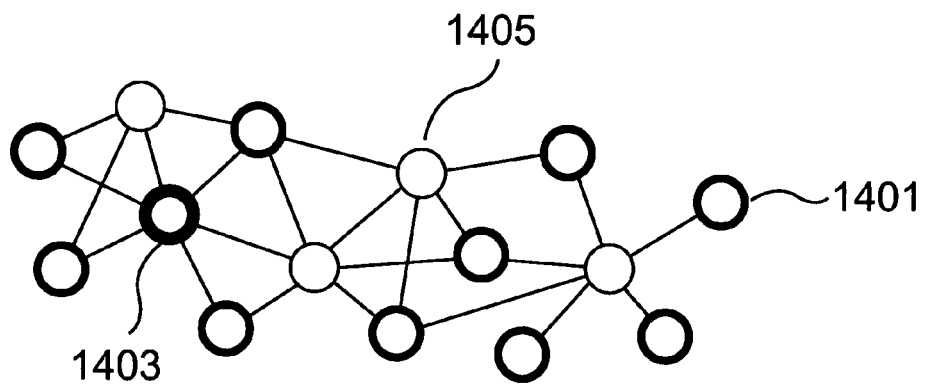
O Reduced Function Device
  (Sensor Controller, Actuator, etc.)
● PAN Coordinator
O Full Function Device
  (Performs network routing functions)

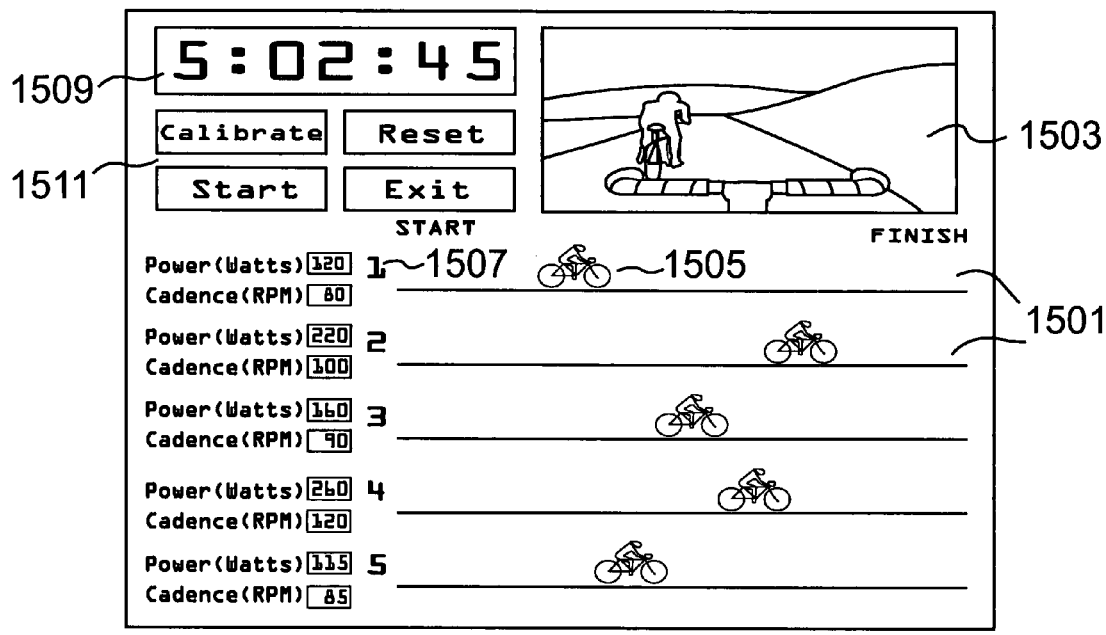
FIG. 15 Illustrative non-limiting example display.

APPARATUS FOR MEASURING EXERCISE PERFORMANCE

CROSS-REFERENCE TO RELATED APPLICATIONS

This application claims the benefit of priority from U.S. Provisional Application No. 60/806,631 filed Jul. 6, 2006, the entire contents of which are incorporated herein by reference.

TECHNOLOGICAL FIELD

The technology herein relates to a method and apparatus for measuring exercise performance. More specifically, the technology herein relates to methods and apparatus for measuring exercise performance on equipment that includes a rotating surface.

BACKGROUND AND SUMMARY

Running, bicycling, and rowing are all popular forms of athletic activity and exercise. Often, given the necessary space, athletes and exercisers may tie on a pair of shoes and run for miles. People may also, if they have access to a bicycle and bicycle paths or a boat and a river, choose to ride or row for fun, competition and/or exercise. Unfortunately, many places do not have bicycle paths or accessible rivers. Also, people may not have the proper equipment to perform many of these exercises.

Additionally, even if a person is merely exercising for general health or fun, a competitive environment can add a much needed edge and can motivate people to higher levels of performance. Competition, however, requires at least one additional person, with the same or similar type equipment (e.g. to race bicycles, all competitors need to have access to bicycles). This can present another barricade to those wishing to competitively race or exercise, as now an entire additional set of equipment is needed.

Certain advances in technology have made many exercises and sport-like options available to people in the comfort of their living room or a local gym. For example, since the advent of the Johnny G spinning bike in the 1980s, spinning has become a popular method of training. Many gyms offer spinning classes, which may focus on a form of group training, featuring different exercises such as high speed spinning while sitting, high torque spinning while standing, etc. In addition to providing bicycling-like exercise without the need for a bicycle path, these spinning classes, for example, offer people the opportunity to exercise in groups. The group nature of these classes is often cited as one of the reasons for their popularity.

Even in a group, however, cyclists (or people participating in other group sports) may not be provided enough information about their performance and the performance of the others in a group. For example, while everyone may know that everyone in a group exercised for twenty minutes, no one may have a benchmark to compare their performance to that of their peers. Thus, the "competitive" aspect is removed from the group. While some bicycles may provide readouts that allow for post-class comparison of numbers, competition could be increased by providing additional real-time feedback at both the individual and the group level.

While a number of devices have been developed to help, for example, cyclists to monitor their cadence speed and amount of power exerted, few work on stationary bicycles. None of these devices provides a relative measure of performance between one cyclist and other group participants, and none are suitable as add-on components for existing exercise equipment. That is, the known power and cadence measurement devices must be built into the bicycle when assembled, and these devices are typically connected to a processing device via a wire.

In accordance with one exemplary illustrative non-limiting implementation, a sensor device is suitable for assembly into a compact unit that can replace one or more friction devices on existing exercise apparatus.

According to another exemplary illustrative non-limiting implementation, a measurement apparatus interfaces with a piece of exercise equipment's brake pads or other friction device, and may be capable of measuring frictional force and/or rotational speed. On a bicycle, for example, these parameters may be respectively converted to power and cadence. Although many of the non-limiting illustrative examples herein refer to bicycles, they are presented by way of example only, and in no way intended to limit the teachings hereof to bicycles. The method and apparatus hereof can be applied to any exercise device including a rotating surface.

Additionally, in this exemplary illustrative non-limiting implementation, a wireless connection to a computer or other calculation device permits further processing of the data and formatting of an exerciser's progress for display on, for example, an electronic display, such as a screen or monitor. In the group environment, multiple equipment sets may be used simultaneously, permitting users to engage in virtual races and other group activities. Data may also be recorded, processed and stored for future analysis, allowing the exerciser, an instructor or other interested party to monitor the exerciser's progress over time.

With the appropriate connections, people could even sit at home and use an Internet connection to compete against exercisers all over the world. Graphic feedback could provide a real-time competitive environment and allow those who do not have time to attend traditional gym classes an opportunity to nonetheless exercise in an indoor, competitive group environment.

According to a further exemplary illustrative non-limiting implementation, a measurement device can optionally be retrofitted onto existing equipment. Stationary exercise equipment such as bikes, rowing machines and treadmills often carries a hefty price-tag. Many people, especially gyms with limited budgets and home-users, may not want to replace a still-functional piece of equipment. Or, they may want to replace it to gain the benefits of the exemplary implementations, but may not be able to afford to. If one exemplary implementation is capable of being retrofitted to existing equipment, it becomes much less expensive and wasteful for numerous people to participate in group exercises as presented herein.

In accordance with a desire to make the device convenient and unobtrusive, one exemplary illustrative non-limiting implementation is provided with a wireless connection to a processing device, such as a computer. In this exemplary implementation, there is no need to run bulky and potentially hazardous wiring from one or more pieces of exercise equipment to a processing device.

According to another exemplary illustrative non-limiting implementation, each sensor device may have an individual identification. This ID can be, for example, an alphanumeric code, a detachable memory device or card, or any other suitable form of unique identification.

In yet another exemplary illustrative non-limiting implementation, a sensor device senses at least the frictional force of a brake pad onto a wheel. Alternatively or additionally, the sensor device may also sense the frequency of rotation of the wheel. Other appropriate measurements, such as leaning and heart-rate may also be taken through the same or additional sensor devices. The sensed parameters may be coupled to a visual feedback environment that informs the exerciser of his or her current performance. Possible performance parameters include, but are not limited to, relative location on a virtual course and to other exercisers, time, power, cadence, heart-rate, distance, velocity, work, etc.

As one example, a group of people can be tracked in virtual proximity based on their individual speed or other outputs. Through the use of, for example, a leaning sensor, it may even be possible to encourage realistic leaning or movement when passing a cyclist or rounding a virtual corner. The visual displays can be shown on a TV display, a computer monitor or other appropriate display as static or moving graphics. Displays can also be forgone if there is only a desire to measure, for example, individual performance. The competitors may be in the same room (such as at a gym), or may be in locations spread out all over the world and connected over the Internet.

BRIEF DESCRIPTION OF THE DRAWINGS

These and other features and aspects of the exemplary illustrative non-limiting implementations will be better and more completely understood by referring to the following detailed description of exemplary illustrative non-limiting implementations in conjunction with the drawings of which:

FIGS. 1A-B show exemplary illustrative exercise equipment;

FIG. 10 shows another exemplary block diagram of the hardware shown in FIG. 9;

FIG. 11 shows an exemplary flow of exemplary system software;

FIG. 12 shows an exemplary state diagram of an exemplary software flow of an exemplary main processing device;

FIGS. 13 and 14 show exemplary network layouts for multiple device connectivity; and FIG. 15 shows an exemplary illustrative display with a virtual map of various participating cyclists.

DETAILED DESCRIPTION OF THE ILLUSTRATIVE IMPLEMENTATIONS

While the exemplary illustrative non-limiting implementations may be applied to many different types of exercise equipment, example is provided herein, by way of explanation, not limitation, of the application to an exercise bicycle. Exercise bicycles 101, 111 such as those shown in FIGS. 1A and 1B, typically provide resistance to pedal motion via a rotating surface 103 that is impeded by a frictional device such as a brake pad 113 or strap 105.

Figure 2:
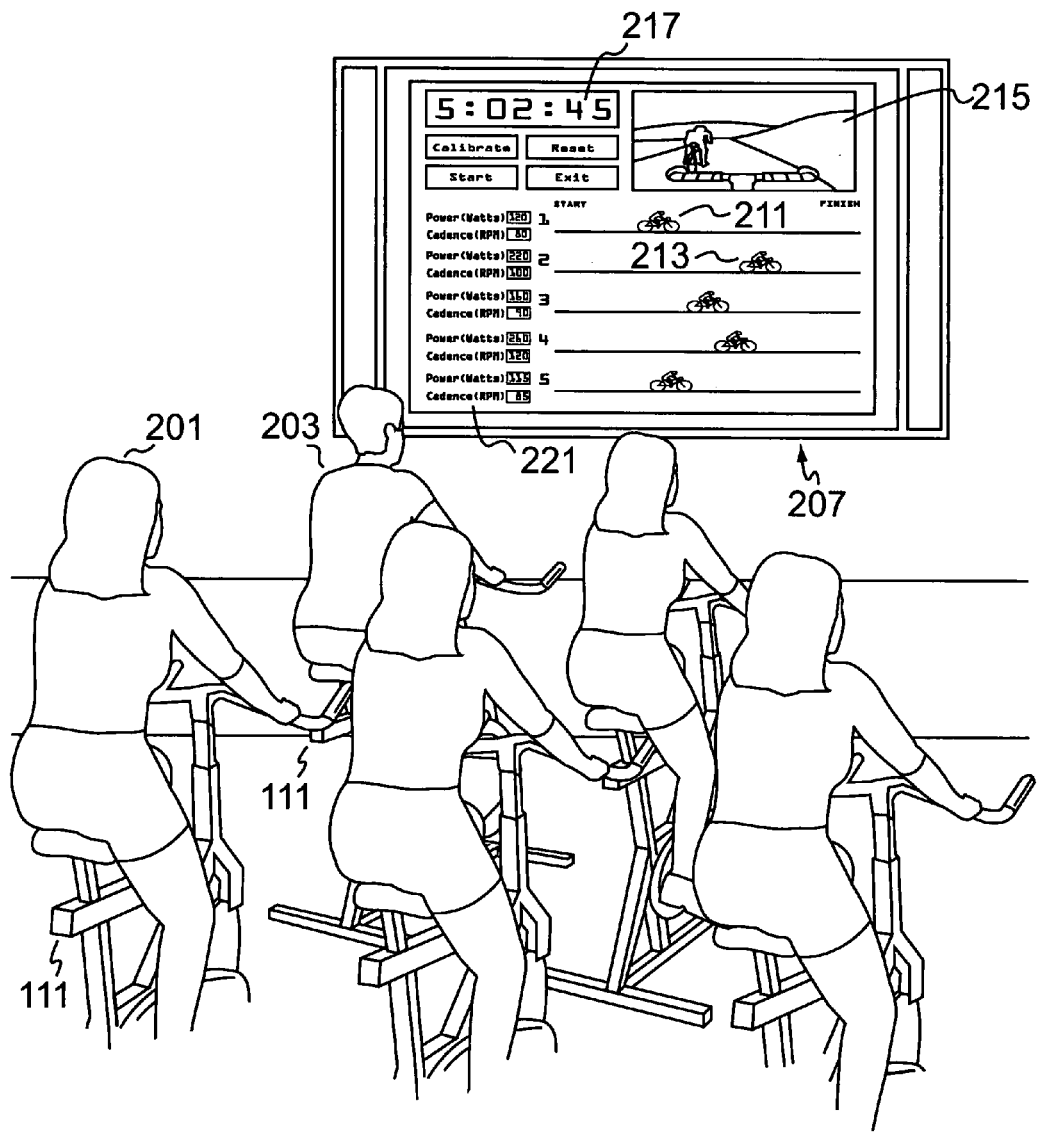
FIG. 2 shows exemplary illustrative exercise equipment being used in a group environment.

Such bicycles are often used in group environments or classes, such as shown in FIG. 2. In FIG. 2, a plurality of participants 201, 203 are exercising together on exercise bicycles 111 provided with sensor devices (not shown). Based on feedback from the sensor devices, a display 207 shows each of the participants a variety of information about the exercise session. For example, a total time or possibly a clock 217 can be shown at one position on the display 207. Additionally, visual feedback as to the composition of the group can be provided in a display of a virtual environment 215. Each participant's relative position may also be shown. Here, position indicator 211 corresponds to participant 201 and position indicator 213 corresponds to participant 203. A variety of additional information 221 can also be shown about each participant.

It may be desirable to show some or all of this information on an individual basis. To the extent that private displays are available for each participant, the virtual environment 215, for example, may be shown to each participant from their own personal perspective (i.e. as if they were at a certain position within the environment).

Overall System

In accordance with one exemplary illustrative non-limiting implementation, a sensor device may be utilized on a single piece of equipment or in groups of similar or dissimilar equipment. Individually or in groups, the sensor device(s) may communicate wirelessly to one or more processing devices. These processing devices may also be used to store incoming data and also display information in real time or at a time of a user's choosing.

Figure 3:
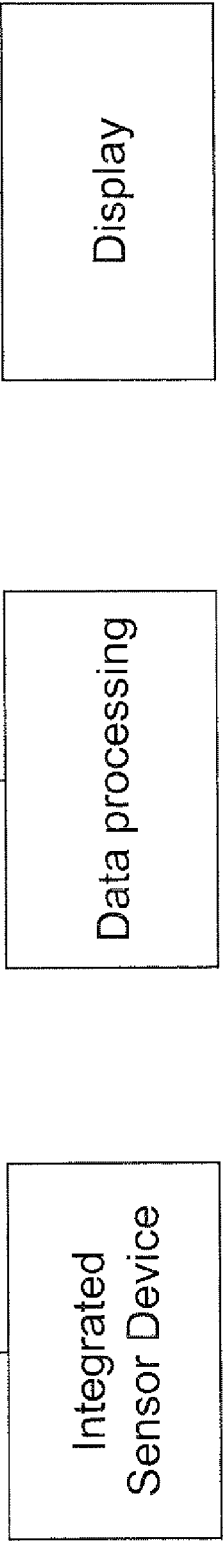
FIG. 3 shows an overview of exemplary components of an exemplary integrated sensor system.
Figure 8:
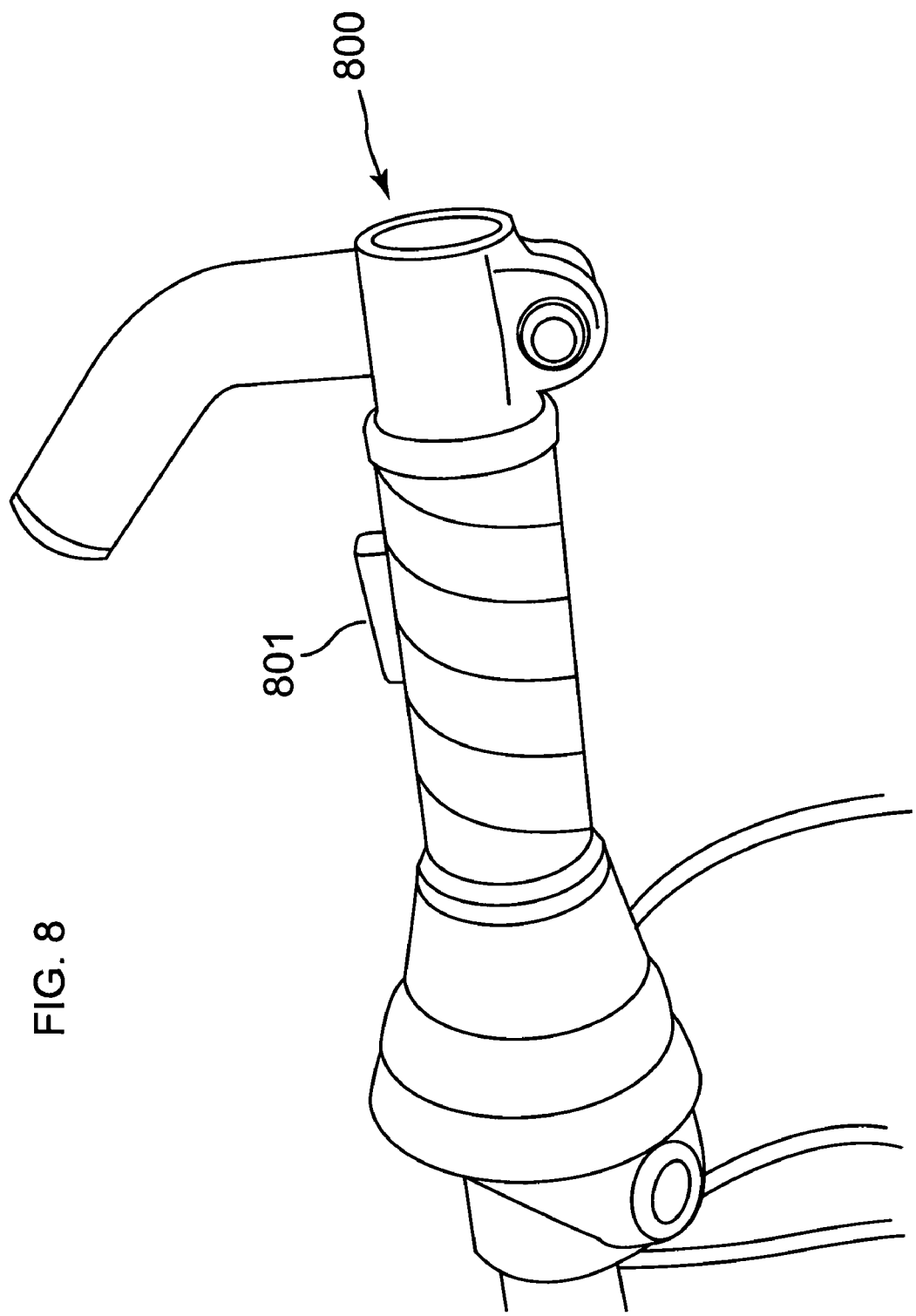
FIG. 8 shows an exemplary illustrative leaning sensor.

An exemplary illustrative non-limiting implementation of a system shown in FIG. 3 consists of three main components: An integrated sensor device 301, a data processing device 311, and a display 321. By way of example without limitation, the integrated sensor device may include a cadence sensor, a force sensor, a processing unit and a wireless transceiver. Additional sensors may include, but are not limited to, leaning sensors (an example of which is shown in FIG. 8), a heart-rate monitor, and other additional sensors.

The data processing may include, but is not limited to, firmware, hardware, software and other processing and output components. Data processing may be performed partially on the integrated sensor as well as on the main workstation, which may also hold the software for the display. Data processing tasks may include filtering the data, sampling the data, sending the data to the main workstation and converting the data to a proper format which may then be displayed.

Figure 4:
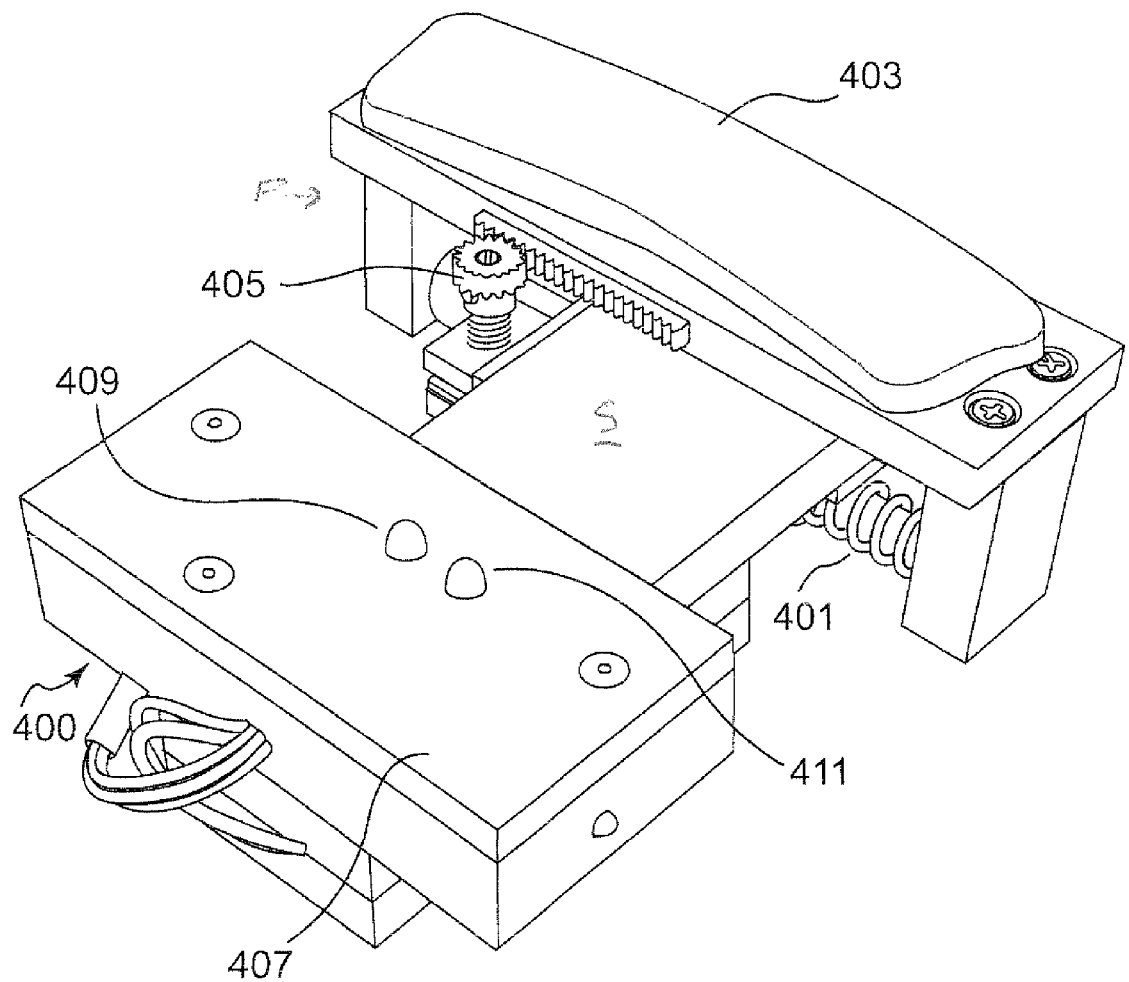
FIG. 4 shows an exemplary illustrative implementation of an integrated sensor device.
Figure 5:
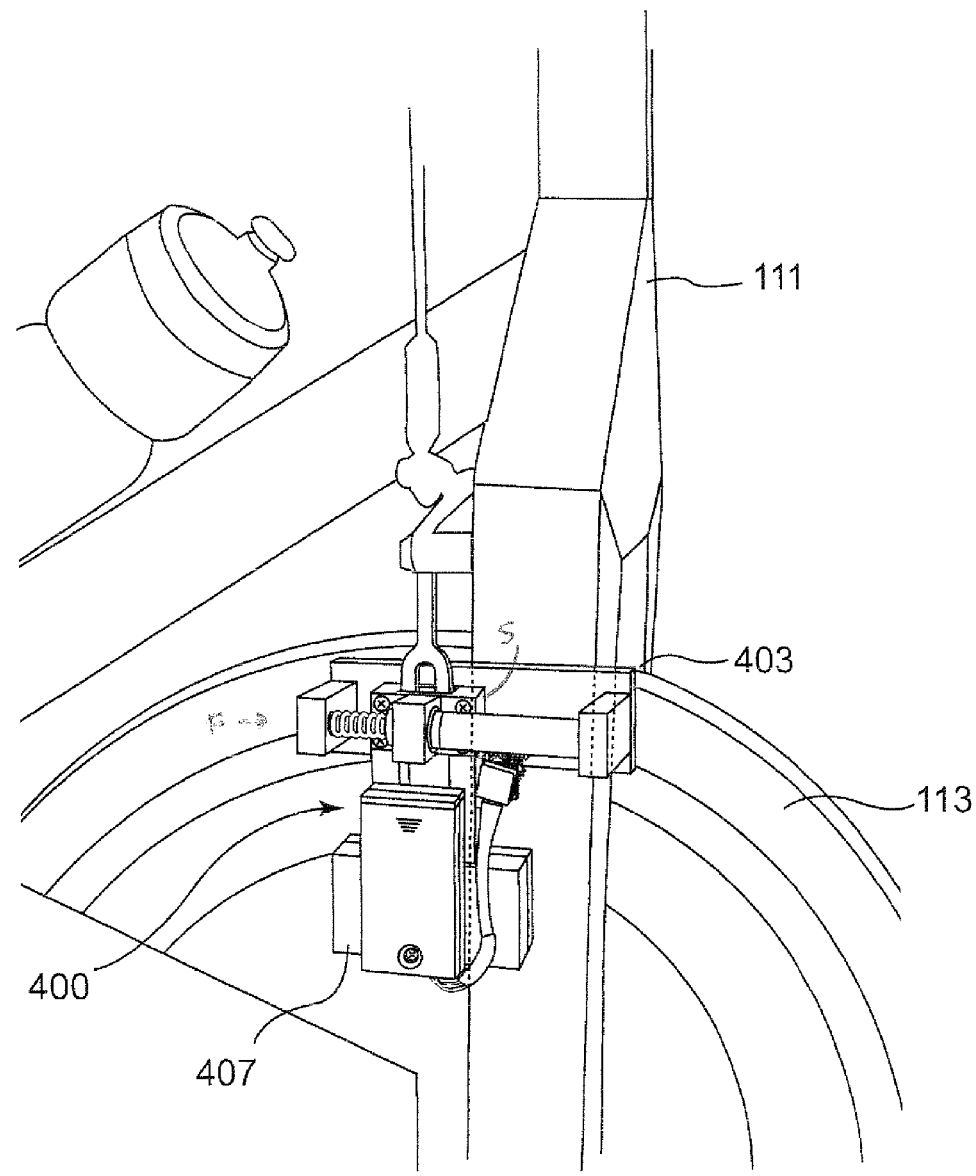
FIG. 5 shows the exemplary illustrative sensor device of FIG. 4 mounted on an exemplary piece of exercise equipment.

An exemplary illustrative non-limiting implementation of a sensor device 400 is shown in FIG. 4 and FIG. 5. This implementation includes a structure S providing a force sensor F equipped with a brake pad 403. The brake pad 403 can make frictional contact with a rotating wheel 113 (shown in FIG. 5) to measure force being applied to the wheel. A compressible spring 401 can be used to bias the brake pad 403 into a neutral position. Force applied to the brake pad 403 can be detected through the rotating cog 405. This implementation also includes a cadence sensor 407. The protrusions 409, 411 are optical outputs and inputs. This is just one example of an assembly that can detect force applied to a wheel, and any suitable assembly may be used.

FIG. 5 shows an exemplary illustrative non-limiting implementation of a bicycle 111 outfitted with an exemplary sensor device. The wheel 113 contacts the brake pad 403 when the sensor device 400 is installed. The inputs and outputs of the optical sensor 407 cannot be seen here as they are facing the wheel 113.

Figure 6:
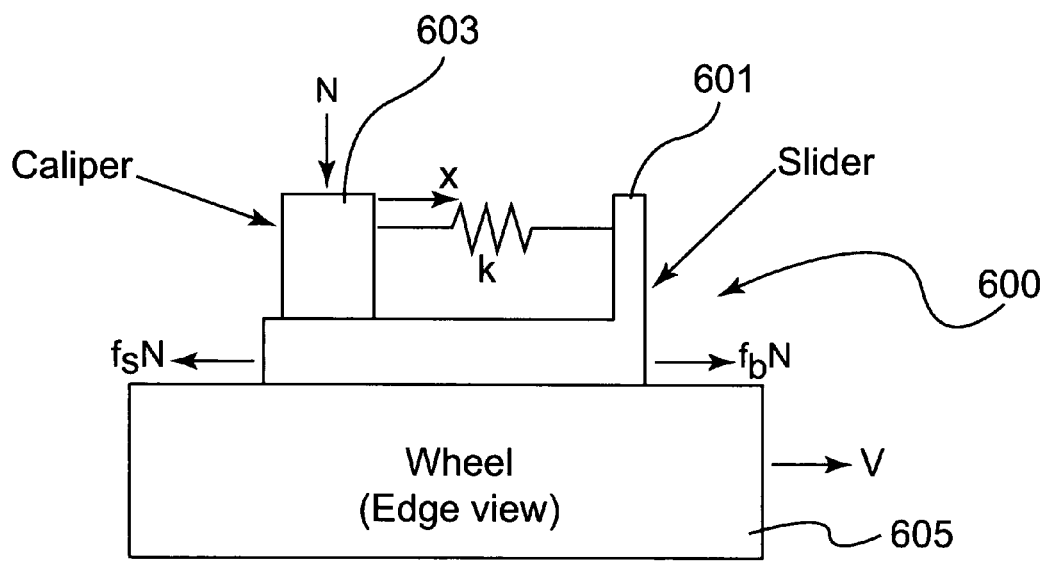
FIG. 6 shows an exemplary illustrative integrated force sensor and brake design.

FIG. 6 shows an exemplary illustrative non-limiting implementation of a sensor device which measures frictional force exerted on a rotating surface using a force sensor. This sensor can replace a part of the exercise bicycle providing resistance for the exercise bicycle.

Force Sensor

According to one exemplary illustrative non-limiting implementation, the force sensor 600 may be mechanically coupled to a friction device of the exercise equipment and use the braking force to determine power output. For example, if the friction device is a brake, the braking mechanism applies a normal force, N, to the brake pad of friction coefficient $f_b$. This applies a force, F, to the wheel moving at some transverse velocity, V. For a simple brake:

$$F = N f_b \tag{1}$$

As shown in FIG. 6, the exemplary illustrative non-limiting implementation uses a slider 601 or other low-friction design that is being pressed into the rotating surface 605 by the brake caliper 603 or other device. The slider position, x, relative to the caliper is determined by a spring having spring constant k. The coefficient of friction between slider and brake $f_s$.

The governing equation for the force F applied to the wheel 605 is:

$$F = f_b N = k\Delta x + f_s N \tag{2}$$

Note that the normal force, N, enters into the equation, but this force may not be known. Thus, $f_s$ may be kept small so as to render the second term of the above equation small compared with the overall force. Specifically:

$$f_b \gg f_s \tag{3}$$

The ratio of friction coefficients may also have an effect on system performance. The ration is defined as:

$$\alpha = \frac{f_s}{f_b} \tag{4}$$

Substituting α into the second equation and solving for N provides:

$$N = \frac{k\Delta x}{f_b} + \alpha N \tag{5}$$

$$N = \frac{k\Delta x}{f_b(1-\alpha)}$$

Using this to solve for F yields, $$F = k\Delta x + \frac{f_s k\Delta x}{f_b(1-\alpha)} \tag{6}$$

$$F = \frac{k\Delta x}{1-\alpha}$$

If α is known and is less than 1, then the equation may be solved. Friction coefficients are seldom well-defined and often change over time due to changes in the environment or mechanical wear. In this case, one would especially expect the brake coefficient of friction to change over time since it is both exposed to the environment and subjected to much more wear than the slider. The error in α is defined as ε and may be expressed in terms of the error in the brake friction coefficient:

$$\alpha + \varepsilon = \frac{f_s}{f_b + \varepsilon_b} \tag{7}$$

Solving for the error in α gives:

$$\varepsilon = \alpha \left( \frac{1}{1 + \frac{\varepsilon_b}{f_b}} - 1 \right) \tag{8}$$

Taking the derivative of equation 6 with respect to α helps show how the slope of F varies as a function of α.

$$\frac{dF}{d\alpha} = -\frac{k\Delta x}{(1-\alpha)^2} \tag{9}$$

Thus, where α is small, the change in force with α is also very small. For example, where α is 0.1, a doubling of α produces a roughly 12% change in force. Where α starts at 0.25, the same doubling results in a 50% change and a similar absolute change of 0.1 results in a force change of 15%. Thus, keeping α small achieves good measurement accuracy.

Cadence Sensor

Figure 7:
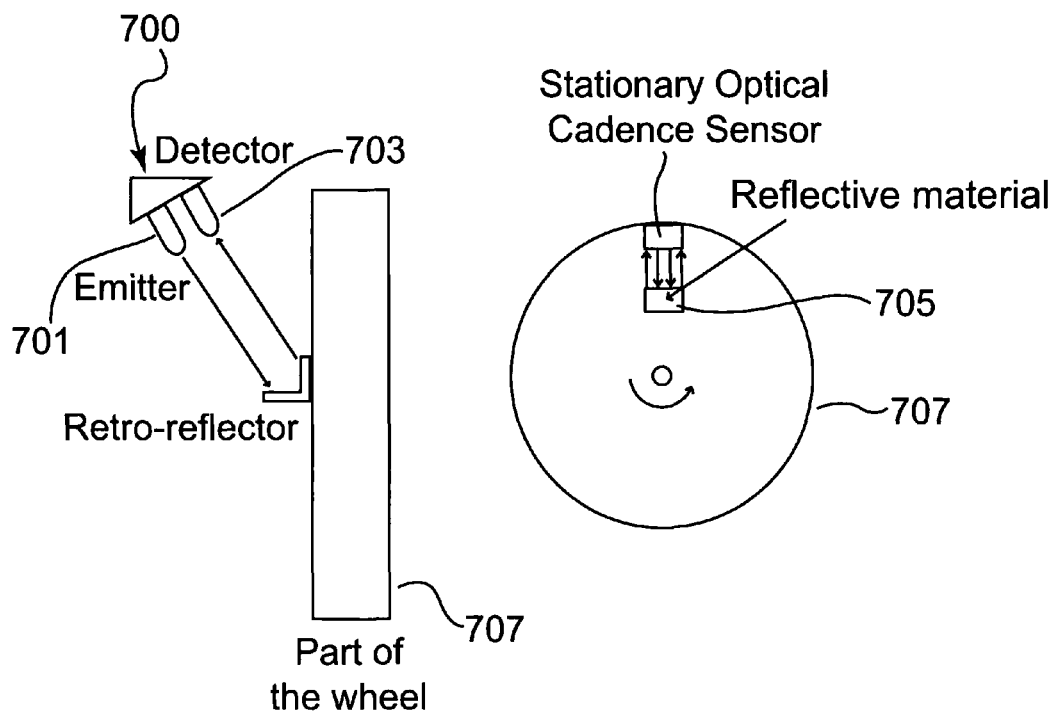
FIG. 7 shows an exemplary illustrative optical cadence sensor.

The cadence, or spinning surface rotation rate, may be measured by many different types of devices such as a potentiometer, magnetic sensor, optical encoder, mechanical encoder or other optical device as shown in FIG. 7. The exemplary illustrative non-limiting implementation shows an integrated sensor device utilizing an optical sensor. The optical cadence meter approach is one implementation that can be assembled at low costs, implemented in exercise equipment containing ample ferrous materials (which may interfere with magnetic solutions) and is amendable to being packaged in a compact housing along with other exemplary illustrative components as described herein. A typical optical sensor 700 consists of an emitter 701, a detector 703, and a piece of reflective material 705 on a rotating surface 707.

The reflective material 705 may be a retro-reflector, which reflects light only in the direction from which it originates. As the wheel 707 rotates, the retro-reflector 705 passes the emitter 701 and reflects its light back into the detector 703. The detector 703 shows a voltage drop monitored by the microprocessor and converted into a frequency and cadence, where frequency is measured in Hertz and cadence in revolutions per minute.

FIG. 8 shows an exemplary illustrative non-limiting implementation of a leaning sensor 801. Since most stationary bicycles do not lean or have the appropriate pieces to support "simulated" leaning, FIG. 8 shows an exemplary leaning sensor 801 provided on a handle 800 of a stationary bicycle. One of these sensors could be provided on each handle, and when a user wants to "lean" the user could press the sensor on the appropriate side. Additional types of sensors could also be used to detect leaning, including more advanced sensors that detect shifts in weight distribution (deployed under a seat, for example).

The Embedded Hardware

Figure 9:
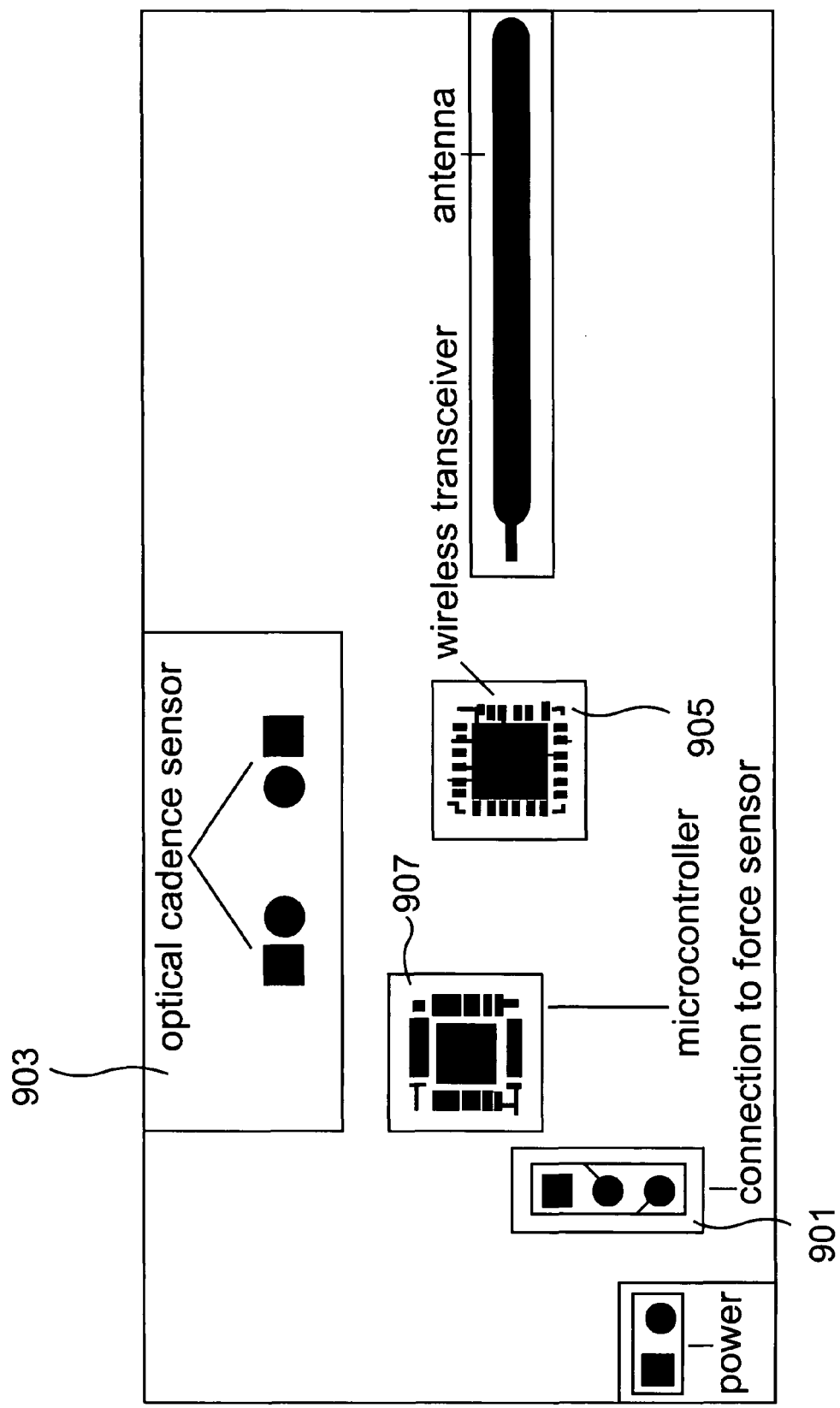
FIG. 9 shows an exemplary block diagram of a physical layout of exemplary electronic hardware components of an exemplary sensor device.

According to an exemplary illustrative non-limiting implementation, the sensor device includes a force sensor 901, a cadence sensor 903, a microcontroller 907 and a wireless chip 905 as shown in FIG. 9. Additional hardware signal conditioning may also be included between the sensors and the microcontroller input ports. Additionally or alternatively, the signal conditioning may be performed in the software.

The microcontroller may perform the following functions, among others:

1.) Converting analog signal levels into digital numbers.
2.) Performing digital filtering to remove electrical and mechanical noise.
3.) Measuring the time between voltage drops (1/frequency of rotation) and the value of the potentiometer reading (which may be converted to force by a processing device).
4.) Controlling the communication of these values to a central site through a wireless network.

An exemplary block diagram of an exemplary sensor device is shown in FIG. 10. In this exemplary block diagram the system includes a cadence sensor 1001 and a force sensor interface 1003. The signals from the sensors 1001 and 1003 are sent to an exemplary signal conditioning program 1005 and then to a microcontroller 1007. The microcontroller, in this implementation, is in bi-directional communication with a wireless chip 1009 connected to an antenna 1011. The antenna is provided to transmit to a processing device.

FIG. 11 shows an exemplary illustrative non-limiting state flow of exemplary embedded software. The microcontroller starts by initializing sensor values and wireless configurations (1101). After initialization, the microcontroller enters a loop. First, the microcontroller checks to see if a ping is received (1103). A ping is a message that tells the device when to start monitoring and sending the sensor data. If the microcontroller does not receive a ping after a set amount of time, a search timeout may be detected (1107). If no search timeout is detected, the microcontroller attempts to detect if a channel is open (1111). If this is not found, the loop goes back to a ping.

If a ping is detected, sensor data is sent to the chip (1105). At the chip, if the data is read, the latest data is stored (1115). If a timeout is detected, a wireless channel is opened (1109). On the next loop, the open wireless channel will be detected at step 1111 and the software will go into a sleep mode (1113).

Bi-directional communication may be implemented to ensure that data reaches the central site and that all bicycles can communicate.

An exemplary illustrative state-diagram showing the control of the system through a processing device is shown in FIG. 12. First, the processing device creates a display (1201) such as that shown in FIG. 15. Then, the processing device may ping one or more integrated sensor devices to establish a connection with each sensor to be used during a particular competition or exercise (1203). If a controlling user selects a calibrate button from a menu, the processing device may request that all participants remove a resistance or set a resistance to the lowest value and then calibrates the sensors (1207). Then, the controlling user may start the session. The processing device then starts to collect data from each bicycle, processes it and may display it (1209). At any time, the controlling user may choose to exit or reset the process.

Additionally, each sensor may have some means of uniquely identifying each user, such as a hardwired ID, a set of switches, a code, or a card or some other device a participant can interface with the sensor device.

Although a substantial number of pieces of exercise equipment may be connected to a central site, the low data rate typical of low-power transceivers (approx 3 bytes/second/transceiver) may be equivalent to a total transmission rate of less than 10 kbits/second for 256 bikes in one room.

Although the network can be set up in a variety of fashions, two exemplary non-limiting implementations of possible network configurations are shown in FIGS. 13 and 14. FIG. 13 shows an exemplary star topology network where a plurality of devices 1301 (e.g. sensors) are connected to a central controller 1303. In FIG. 14, an exemplary mesh network is shown. The mesh network has a controller 1403 and a plurality of devices 1401 (e.g. sensors). In the mesh network of FIG. 14, one or more routing devices 1405 are also included.

Display

In addition to processing information from individual participants, the processing device may also include an output to a display. One exemplary illustrative non-limiting implementation of a display is shown in FIG. 15. The display can provide information to users, leaders and onlookers, to educate, motivate and entertain them. Many forms of display and pieces of information may be possible. As shown in FIG. 15, a map of cyclist position 1501 provides visual feedback to participants about their individual positions in a simulated race. A view of the virtual world 1503 can also provide feedback to participants about the layout of the course ahead.

According to this illustrative exemplary non-limiting implementation, the display also includes icons 1505 and/or numbers 1507 corresponding to a symbol on each bicycle. Current race time 1509 can also be shown, and it can be seen who is a leader either by looking at the icons 1501 and/or a visual notification of the leader symbol or ID. A variety of menu options 1511 may also be shown, for use by a controlling participant. This controlling participant is typically a group leader, but any participant can be given control.

Additional non-limiting options may include: the ability to look at certain groups of cyclists, a display of a map or scenery, a storage of the information of each cyclist for later retrieval, a real-time display of comparison of force setting between the cyclists and the group leader, additional handicap settings for participants, etc. Commercial scenic display software can also be implemented into the display, to allow participants to engage in exercise in a variety of virtual environments (e.g., they could race through the streets of Paris, etc.).

Often, these devices will be used in, for example, an exercise class. In such a class, a predetermined group leader is typically present. Since the leader can, through the menu, easily visually see where in the pack specific participants fall, the leader can then more easily provide encouragement for those participants. This encouragement can be verbal encouragement or could even take the form of a menu selectable option. For example, the leader could choose to see a select group of participants and easily determine what their respective cadences were. If participant #3 is lagging behind, the leader could vocally encourage #3, or could click on, for example, an "encourage" option, which may send a message to a personal display on the equipment of #3 or may even display a message on a main display visual by all participants.

This could have additional functionality if, for example, a leader in one location was leading groups of participants at several additional remote locations. This allows the leader to track and encourage performance even if they are not physically present, and allows the participants to know that the leader is still giving personal attention to their individual performances.

Further, all participants may have a summary of their individual performances printed out, including graphical analysis. The information can be collected over many sessions with a detailed analysis of the performance.

While the technology herein has been described in connection with exemplary illustrative non-limiting implementations, the invention is not to be limited by the disclosure. The invention is intended to be defined by the claims and to cover all corresponding and equivalent arrangements whether or not specifically disclosed herein.

We claim:

1. An integrated sensing and braking component, for use with an exercise machine of the type that permits a human exerciser to spin a wheel, said integrated sensing and braking component removably attachable to said exercise machine and configured to apply friction to the spinning wheel of the exercise machine and to measure power the human exerciser manually expends to spin said exercise machine spinning wheel, said integrated sensing and braking component comprising:

a structure removably attachable to the exercise machine;
 a friction applying component directly mounted to said removably attachable structure, said friction applying component configured to, in use, apply frictional force to said spinning wheel;
 a force sensor directly mounted on the removably attachable structure, the force sensor in use sensing the amount of frictional force the friction applying component applies to the exercise machine spinning wheel;
 a cadence sensor directly mounted on the removably attachable structure, the cadence sensor configured to sense a cadence rate at which said spinning wheel is spinning;
 a processor directly mounted on the structure, the processor coupled to said force sensor and said cadence sensor, said processor calculating power at least in part in response to said sensed force and said sensed cadence rate; and
 a transmitter directly mounted on the structure and coupled to the processor, the transmitter wirelessly communicating at least one data packet representing said calculated power to a location that is remote to said structure.

2. The integrated sensing and braking component of claim 1, wherein:

the cadence sensor comprises an optical sensor configured to sense at least rotation speed of the spinning wheel on which at least one reflector is disposed, and
 the contents of the at least one data packet transmitted by the transmitter are at least partially dependent on the rotation speed detected by the optical sensor.

3. A group sensor feedback system comprising:

plural integrated sensing and braking components as claimed in claim 1, wherein each said integrated sensing and braking component is removably attached to a different exercise machine;
 at least one group processor that generates a display signal output;
 a receiver coupled to the group processor; and
 at least one group display that displays the group processor display signal output;
 the receiver being configured to receive signals transmitted by the plural integrated sensing and braking components;
 the group processor processing signals received by the receiver and in response thereto, outputting the display signal output to the at least one group display;
 the at least one group display providing graphical feedback indicative of the signals transmitted by the plural integrated sensing and braking components to encourage group competition.

4. The sensor feedback system of claim 3, wherein the graphical feedback includes a scenic display showing a virtual view including a representation of at least one person exercising.

5. The sensor feedback system of claim 3, wherein the graphical feedback provides images indicative of plural people exercising and shows relative positions of the people traveling respective virtual distances.

6. The sensor feedback system of claim 3, wherein the graphical feedback includes a graphical representation of power.

7. The sensor feedback system of claim 3, wherein the graphical feedback includes a graphical representation of cadence.

8. The sensor feedback system of claim 3, wherein the graphical feedback includes a representation of total exercise time from a start time of a session.

9. The sensor feedback system of claim 3, wherein the graphical feedback includes a menu having choices selectable by at least one user of a group of plural users each using exercise machines.

10. The integrated sensing and braking component of claim 1 wherein said removably attachable structure is configured and dimensioned to be removably attached to the exercise machine in substitution for a brake pad.

11. The integrated sensing and braking component of claim 1 wherein the friction applying component comprises a passive brake pad engaging the spinning wheel, the user manually controlling, in use, the passive brake pad to apply a variable amount of friction to the spinning wheel of the exercise machine.

12. The integrated sensing and braking component of claim 1, wherein the force sensor comprises a displacement sensor that senses displacement of the friction applying component against a bias, the displacement caused by spin of the spinning wheel, said displacement being indicative of a controllable amount of friction the friction applying component applies to the spinning wheel.

13. The integrated sensing and braking component of claim 1 wherein the at least one friction applying component comprises a brake pad.

14. An integrated sensing and braking component for being removably attached to an exercise machine of the type that permits a human exerciser to spin a wheel by manually pedaling foot pedals coupled to the wheel, said integrated sensing and braking component comprising:

a structure removably attachable to said exercise machine;
 a brake pad directly mounted to said removably attachable structure, said brake pad in use movably contacting and frictionally engaging the wheel;
 a force sensor directly mounted on the removably attachable structure in communication with the brake pad, the force sensor in use sensing the amount of frictional force the brake pad applies to the wheel;
 a cadence sensor directly mounted on the removably attachable structure, the cadence sensor configured to in use sense a cadence rate at which the wheel of the exercise machine is spinning; and
 a wireless module directly mounted on the removably attachable structure and coupled to the force sensor and the cadence sensor, the wireless module in use wirelessly communicating data responsive to the amount of force measured by the force sensor and the cadence rate measured by the cadence sensor.

15. The integrated sensing and braking component of claim 14 wherein said integrated sensing and braking component is adaptable for field-retrofitting on a exercise machine of the type that permits a human exerciser to manually spin a wheel, the integrated sensing and braking component for being removably attached to the exercise machine in place of a mechanical brake pad of the exercise machine.

* * * * *